US006745070B2

United States Patent
Wexler et al.

(10) Patent No.: US 6,745,070 B2
(45) Date of Patent: Jun. 1, 2004

(54) HIGH DEFINITION ELECTRICAL IMPEDANCE TOMOGRAPHY

(75) Inventors: Alvin Wexler, Winnipeg (CA); Zhen Mu, Chelmsford, MA (US); Rajen Manicon Murugan, Austin, TX (US); Guye S. Strobel, Vienna (AT)

(73) Assignee: Tasc Ltd., Winnipeg (CA)

( * ) Notice: Subject to any disclaimer, the term of this patent is extended or adjusted under 35 U.S.C. 154(b) by 105 days.

(21) Appl. No.: 09/801,706

(22) Filed: Mar. 9, 2001

(65) Prior Publication Data

US 2002/0138019 A1 Sep. 26, 2002

(Under 37 CFR 1.47)

Related U.S. Application Data

(63) Continuation-in-part of application No. 08/943,131, filed on Oct. 3, 1997, now Pat. No. 6,201,990.
(51) Int. Cl.$^7$ ............................................. A61B 5/053
(52) U.S. Cl. ..................... 600/547; 324/326; 324/357; 324/600
(58) Field of Search .................. 600/547; 324/323–326, 324/347, 354, 357, 600

(56) References Cited

U.S. PATENT DOCUMENTS

| | | |
|---|---|---|
| 5,272,624 A | 12/1993 | Gisser et al. |
| 5,284,142 A | 2/1994 | Goble et al. |
| 5,465,730 A | 11/1995 | Zadehkoochak et al. |
| 5,544,662 A | 8/1996 | Saulnier et al. |
| 5,626,146 A | 5/1997 | Barber et al. |
| 5,807,251 A | 9/1998 | Wang et al. |
| 5,919,142 A | 7/1999 | Boone et al. |

*Primary Examiner*—Ruth S. Smith
(74) *Attorney, Agent, or Firm*—Shapiro Cohen

(57) ABSTRACT

A method of imaging an object contained in a medium, having a specific impedance which is different from the specific impedance of the medium, comprising applying current to the medium at various locations at a surface of the medium, extracting current at other locations, detecting voltages produced by the current which has passed through the medium from the surface of the medium at various other locations, successively determining a location and shape and conductivity of the object with increasing accuracy by processing values of the detected voltages, determining a region in the medium in which the object is located from values of the detected voltages which are within upper and lower threshold values, applying acceleration procedures to the conductivities within the region in the course of iterative refinement of these values in the course of an imaging procedure, subsequently restricting further determination of the location of the object with increasing accuracy to voltages obtained from the region of the medium in which the object is located, and displaying an image on an axis using the restricted location determination values.

2 Claims, 11 Drawing Sheets

20 ITERATIONS FOR
ORIGINAL ALGORITHM

5 ITERATIONS FOR
PEAK DETECTION METHOD

ORIGINAL IMAGE CONTRAST [1:2]

20 ITERATIONS WITH
ORIGINAL ALGORITHM

MODEL 2.00
1.95
1.90
1.85
1.80
1.75
1.70
1.65
1.60
1.55
1.50
1.45
1.40
1.35
1.30
1.25
1.20
1.15
1.10
0.95

RESULT

| PHYSICAL ARRANGEMENT | IDEAL RECOVERED IMAGE | ACTUAL RECOVERED IMAGE |

HIGH DEFINITION ELECTRICAL IMPEDANCE TOMOGRAPHY

The present application is a continuation in part of prior application Ser. No. 08/943,131 filed Oct. 3, 1997, now U.S. Pat. No. 6,201,990 dated Mar. 13, 2003.

FIELD OF THE INVENTION

This invention relates to improved methods of detecting and imaging an object or objects contained in a medium which object or objects have contrasting electrical conductivity and/or specific impedance compared to the medium.

BACKGROUND TO THE INVENTION

It was reported in 1926 by H. Fricke and S. Morse in the article "The electric capacity of tumours of the breast", (1926) J. Cancer Res. 16, pp. 310–376 that the electrical properties of breast tumors differ significantly from healthy tissue. Until now it has not been possible to use these properties to detect breast tumors in a manner useful in a clinical setting. However, some laboratory and imaging techniques have evolved.

Electrical Impedance Tomography (EIT) is an imaging methodology that is based upon electrical conductivity or impedance contrasts within the human body. EIT has been the subject of considerable attention recently but, generally, methods used for image recovery have yielded only low-resolution results.

U.S. Pat. No. 4,539,640, issued Sep. 3, 1995, to inventors Bradley Fry and Alvin Wexler (referred to below as the Wexler et al patent), and the article by A. Wexler, B. Fry and M. R. Neuman, entitled "Impedance-Computed Tomography: Algorithm And System". Applied Optics, Vol. 24, No. 23, Dec. 1, 1985-pp. 3985–3992, describe a method and embodiment of a system that solved electromagnetic field equations that govern current flow in a conductive medium, and concurrently extracted an image of the interior of the medium based on the electric current conductivity (and, more generally, specific impedance) distribution in the medium. This provided a methodology for the correct mathematical solution of the inverse (imaging) problem and construction of electronic equipment for this purpose. The method also provided for the accommodation of a great number of pixels through the use of spa-matrix techniques. U.S. Pat. No. 4,539,640 is incorporated herein by reference.

This methodology embodies a number of technological features, e.g. uses a well-conditioned, least-squares method, uses true three-dimensional field solving for images and conductivity values and for identification of characteristic pathologies, is applicable to complex impedance as well as to purely conductive imaging, it allows for application of known CT-based reconstruction methodologies and image processing operations between iterations, only simple contact of electrodes to the skin or to geophysical or other surfaces is sufficient to provide for contact and spreading resistance, it results in a sparse-matrix formulation for high-definition imaging, parallel data acquisition may be performed through frequency multiplexing for speed, and parallel image reconstruction may conveniently be accommodated.

EIT uncovers objects within a host medium by solving for resistivity (or, more generally, specific impedance) distributions within the body. Various techniques have previously been used that treat the flow of applied electrical currents as though they behave in a manner similar to X-ray beams. With this assumption, algebraic reconstruction techniques (ART) originally described by Gordon, Bender and Herman in the article "Algebraic Reconstruction Techniques (ART) For Three Dimensional Electron Microscopy and X-Ray Photography", (1970), J. Theor. Biol. 29, pp 471–481, have been employed by others to uncover a crude approximation of the EIT image.

ART finds wide and accurate use in applications of computed tomography other than EIT. Because electrical currents between any two electrodes flow throughout the body and do not follow ray-like paths, a straightforward application of ART is inappropriate. Therefore, as confirmed by R. H. T. Bates, G. C. McKinnon and A. Seager in the article "A Limitation On Systems For Imaging Electrical Conductivity Distributions", (1980), IEEE Biomed Eng. BME-27, pp. 418, a comprehensive field-solving approach is needed as part of the EIT imaging process.

A considerable body of EIT work has been done at the University of Sheffield in the U.K. Smith, Freeston and Brown describe their Applied Potential Tomography (APT) system which uses a weighted back-projection technique, in "A Real-Time Electrical Impedance Tomography System For Clinical Use—Design And Preliminary Results", (1995), IEEE Trans. Biomed. Eng. BME-42, pp. 133–140.

Guardo et al describe a back-projection reconstruction method which could detect a 3 ml plastic sphere at the centre of a torso-sized cylinder of saline, in "An Experimental Study In Electrical Impedance Tomography Using Back-projection Reconstruction", (1991), IEEE Trans. Biomed. Eng. 38 (7), pp. 617–627. This translates to approximately a 1.5 cm sphere in a 50 cm cylinder.

Shahidi, Guardo and Savard in "Electrical Impedance Tomography: Computational Analysis Based On Finite Element Models Of The Human Thorax With Cylindrical And Realistic Geometries", (1995), Annals Biomed. Eng. 23 (1), pp. 61–69, report that three-dimensional finite element method simulation results show that "a 10 ml edema region with a conductivity equal to that of blood can be detected at a 40 dB signal-to-noise ratio (SNR)", and further: "Detection of a smaller volume, in the order of 2 ml, should be possible by improving either the instrumentation to achieve 60 dB SNR or the performance of the reconstruction methods". These results, scaled to the size of the breast, indicate that even small breast tumors (less than 4 mm in diameter) should detectably alter surface potentials.

It should be noted that detection is not image reconstruction but it is a necessary precondition. Guardo's research team has demonstrated that a practical, measurable signal is available for use in EIT.

Henderson and Webster presented a means for displaying isoadmittance contours of the chest, Tasto and Schomberg described an impedance imaging technique that considers curved current flux tubes and uses back-projection techniques, Lytle and Dines report on the use of impedance techniques for geophysics applications and Price further discusses medical applications and techniques (Henderson, R. and Webster, J. (1978) "An Impedance Camera For Spatially Specific Measurements Of The Thorax", IEEE Trans. Biomech. Eng. BME-25, pp. 250; Tasto, M. and Schomberg, H. (1981) "Method Of And Device for Determining Internal Body Structure", Washington, D.C., U.S. Pat. No. 4,263,920; Lytle, R. J. and Dines, K. A. (1978) "An Impedance Camera: A System for Determining the Spatial Variation of Electrical Conductivity", (1978) Livermore, Calif.: Lawrence Livermore Laboratory Report UCRL-52413; and Price, L. R. (1979) "Electrical Impedance Computed Tomography (ICT): New Imaging Technique", IEEE Trans. Nucl. Sci. NS-26, 2736.

An alternative method as described in the aforenoted U.S. Pat. No. 4,539,640, involves the application of currents to the body and successive measurement of surface potentials. This image recovery method involves the solution of the Poisson/Laplace equation while employing sparse-matrix techniques.

Dijkstra, A. M., B. H. Brown, A. D. Leathard, N. D. Harris, D. C. Barber, and D. L. Edbrooke "Review: Clinical Applications Of Electrical Impedance Tomography", (1993), J. Med. Eng. Technol. 17 (3), pp. 89–98 discuss clinical applications of EIT. They review the conductivity of tissues at around 50 kHz, and show the large contrasts that exist. In their view, ". . . the major disadvantage is the poor spatial resolution which is only about 10% of the diameter of the body. It seems likely that this may be improved to 5% (1 cm in a body of 20 cm diameter) and at this point it begins to be similar to that offered by a gamma camera. We should therefore regard the technique as a monitor of body function and not as an anatomical imaging method."

We believe that this conclusion is pessimistic, as the present invention provides a practical EIT method and apparatus with high resolution that can be used in a clinical setting.

SUMMARY OF THE INVENTION

In one aspect of the present invention, we have developed methods to vastly improve the quality of edge detection at interfaces between surrounding (e.g. breast) tissues and small included objects (e.g. tumors), to accurately and rapidly image small objects and to substantially increase the speed of image extraction. It is believed that this provides a practical method and means that can be used for detection of breast tumors in a clinical setting.

It is known that breast tumor metastasis rapidly increases with tumor size. It has been shown that if all breast tumors are detected and removed by the time they reach 4 mm diameter, total metastasis would be 0.6%, indicating a 99.4% cure rate. We therefore also believe that an effective and relatively inexpensive EIT machine built in accordance with the principles of the present invention, used as a screening tool to find such tumors, could make breast cancer a highly curable disease.

It is believed that by the use of the present invention, imaging of objects that are 5% of body diameter in size are achievable now and it is expected that the method can be used to image objects that are 2.5% of body diameter or smaller. This translates to breast tumors of 5 mm and 2.5 mm respectively. We believe that our new method will provide sufficient spatial resolution to detect tumors smaller than those typically found via mammography.

The principles of the present invention can also be applied to other imaging uses such as subterranean imaging, for the purposes of detection of contamination of groundwater, for location of landmines and other explosives (including those that are plastic encased), etc.

It is expected that use of the present improved methods for the imaging of objects located within bodies in EIT scanners for medical applications will be preferred because they are noninvasive and can be produced relatively inexpensively, as compared to X-ray CT (CAT scan) and MRI (magnetic resonance imaging), and may be operated by trained technicians. For geophysical applications, EIT scanners using the principles of the present invention provide an alternative to test boring and will be able to identify landfill site leachates prior to contamination of groundwater resources. It is believed that they can also be used to image plastic-coated land mines, which otherwise are very hard to find.

In another aspect of the present invention, a method of imaging an object or objects contained in a medium, having a conductivity which is different from the conductivity of the medium, comprises the steps of applying current to the medium at various locations at a surface of the medium, extracting current at various locations, detecting voltages due to currents which have passed through the medium from the surface of the medium at various other locations, successively determining the location and shape of the object with increasing accuracy by processing values of the detected voltages, and determining a region of the medium in which the objects are located from values of the detected voltages.

As a consequence of processing for current values, the method can process for impedance, either resistive or complex.

BRIEF DESCRIPTION OF THE DRAWINGS

A better understanding of the invention will be obtained by a consideration of the detailed description below, in conjunction with the following drawings, in which.

DETAILED DESCRIPTION OF THE PREFERRED EMBODIMENTS

Figure 1:
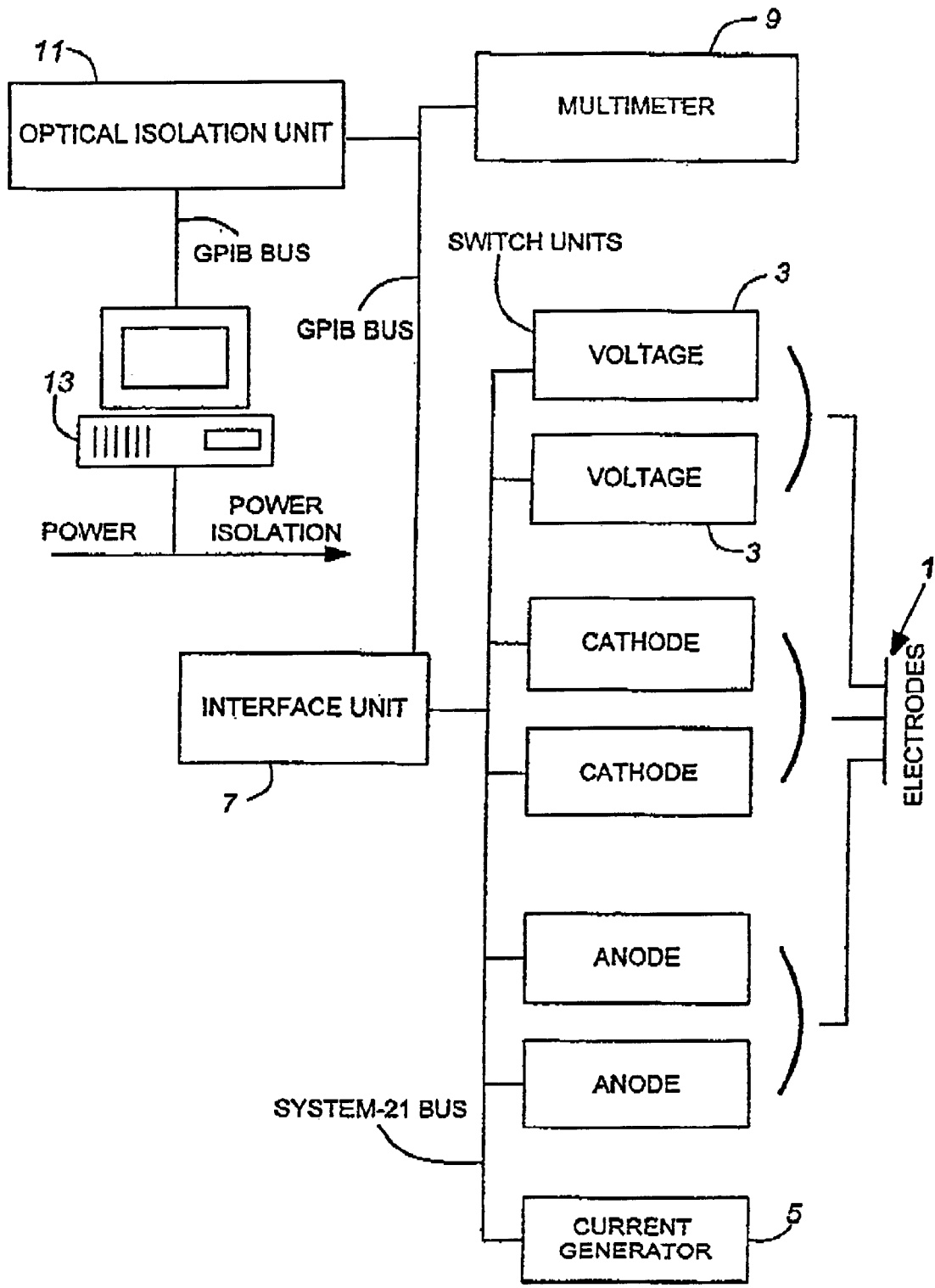
FIG. 1 is a block diagram of a system which can be used to implement the present invention.

FIG. 1 shows a block diagram of a system on which the present invention can be implemented.

The system is comprised of a set of electronic devices controlled by a personal computer. Communication was effected via an IEEE-488 parallel bus to a Fluke/Philips proprietary "System 21" bus using a Philips GPIB interface card installed on the computer. The interface card could address up to 14 GPIB instruments and was hardware and software configured to select an appropriate IRQ setting, DMA channel, and base I/O address.

Plural electrodes 1 for electrically contacting the surface of a medium such as the human body, the earth, etc., are formed into a matrix, and are connected to corresponding electrode selection switches 3. Pairs of electrodes form current injection and extraction sites, and voltage measurement points. The electrodes forming the matrix are disposed along preferably (but not essentially) mutual orthogonal axes x and y. A current generator 5 generates current in any effective waveform, which is applied to predetermined ones of the current injection and extraction sites, and voltage measurement points. The matrix is disposed in a position to overlay a surface of a medium to be analyzed, and to apply and receive current to and from the medium.

The switches 3 also switch the electrodes, to the input of an interface unit 7 which performs analog to digital conversion. The output of the interface unit is connected to a digital multimeter 9, which determines the amplitude of current and voltage received from the respective electrodes. The switch units preferably switch each electrode, to which current is not being applied, in a time-shared manner, to the meter through the interface unit.

In this manner, current is applied to plural places on the surface of the medium, and current is received from other plural places on the surface of the medium after passing through the medium. The interface converts the current to digital form, and is measured with the voltage by multimeter 9.

In a successful embodiment, six banks of twenty switches were used. The switch-banks were grouped in pairs based on their function during the monitoring, e.g. two pair for electrode selection, and a pair for measurement electrode selection. Each electrode served one of the three roles during a single measurement, and many electrodes served in all roles for a complete set of measurements. All units, except the multimeter, were controlled by a master switch unit interfacing between the IEEE bus and the System 21 bus. A controller sent and received data from the units on the System 21 bus by addressing the interface unit 7 and the switch units.

A Philips PM5139 function generator was used as the alternating-current excitation source. Tests were performed to determine the best excitation signal for the medium for in situ monitoring, to be free from distortion, accurately measured, accurately set, and reliably maintained. The system worked best with a current level between 5 and 30 mA, when measuring an object buried in soil.

Switching functions of the system were handled by six separate switch units and the interface device that connected the switch units to the buses. The interface unit was a PM2101 analog to digital converter and formed a simple communication device that resided transparently on the IEEE bus. Access to the switch units was via the GPIB address of the interface unit and the address of the function generator. The interface unit also provided power to the other units.

An optical isolation unit 11 coupled the multimeter 9, via the bus, to a personal computer 13. The personal computer received the digital signals from the multimeter and processed it using the method described below.

Generally, for imaging of objects within soil, a frequency of a few kHz was used for the signal current. At low frequencies, the analysis could proceed as a direct-current analysis. At higher frequencies, complex phasor measurements and analysis techniques are required but, otherwise, the procedure is nearly identical to the direct-current procedure. The generated current can be sine wave in form, or can be of any other effective form, such as square wave, triangular wave, etc.

In a successful embodiment, for imaging of a barrel buried in soil, the conductivity was imaged at 780 points using 38 excitation pairs and 20 electrodes.

Breast imaging should have electrodes substantially surrounding the breast to be imaged, for example by inserting the pendulous breast in a container of saline solution, with the electrodes on the inner surface of the container, thus making it easier to achieve clear results.

The computer 13 processes the signal received from the multimeter in accordance with the process described in U.S. Pat. No. 4,539,640 issued Sep. 3, 1985, invented by Bradley Fry and Alvin Wexler.

However, in accordance with one embodiment of the present invention, referred to in more detail below as the Peak Detection Method, upper and lower thresholds are applied to the values resulting from the processing at various points on the two axis (x,y) plane.

The speed of error function minimization methods can be accelerated by predicting some of the element conductivities according to differences obtained in the early stages of an image recovery procedure. The present invention determines where the prediction should be applied, by use of peak-detection. The method is initially trained by an approximate solution evolving soon after the method begins. Instead of checking conductivity changes for each element, this method takes the entire body as a whole and finds the areas where objects are most likely to exist. Simulation results show great improvements in the speed of convergence and quality of images in cases where adequate contrasts between the background and objects exist.

Figure 2A:
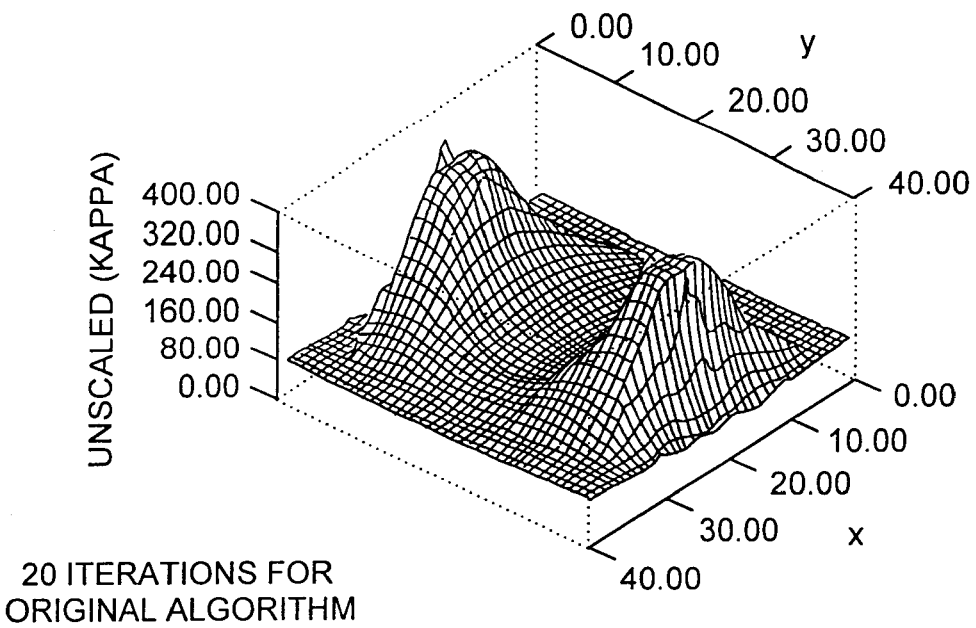
FIGS. 2A and 3A are graphs in three mutually orthogonal axes showing images of conductivity of two, and three objects respectively using a prior art method.
Figure 3A:
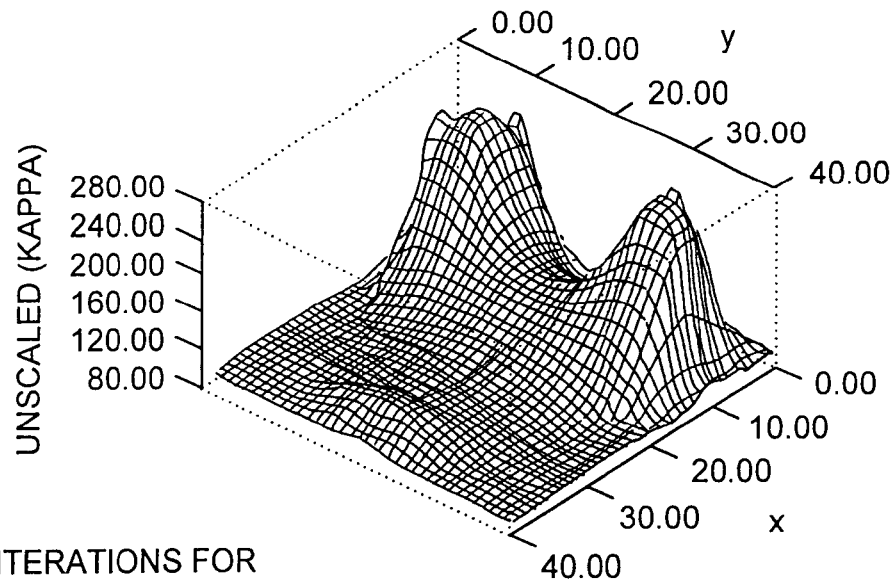

The double-constraint, error-function minimization method—on its own—does not produce an image with sharp edges in a reasonable time. What it does produce is an image with hills of conductivity corresponding to the location of objects, as shown in FIGS. 2A and 3A. FIGS. 2A and 3A illustrate conductivity in a plane, of a recovered image of two objects and of three objects respectively after 20 iterations using the original method. These hills appear regardless of whether the computation is completed for several iterations or for several hundred iterations, i.e. the conductivity improvement directions are defined at a very early stage of computation, picking the local maxima or minima and locating peaks and valleys accordingly. The method in accordance with an aspect of the invention modifies the derivation of images of the element conductivities with an acceleration scheme.

Figure 2B:
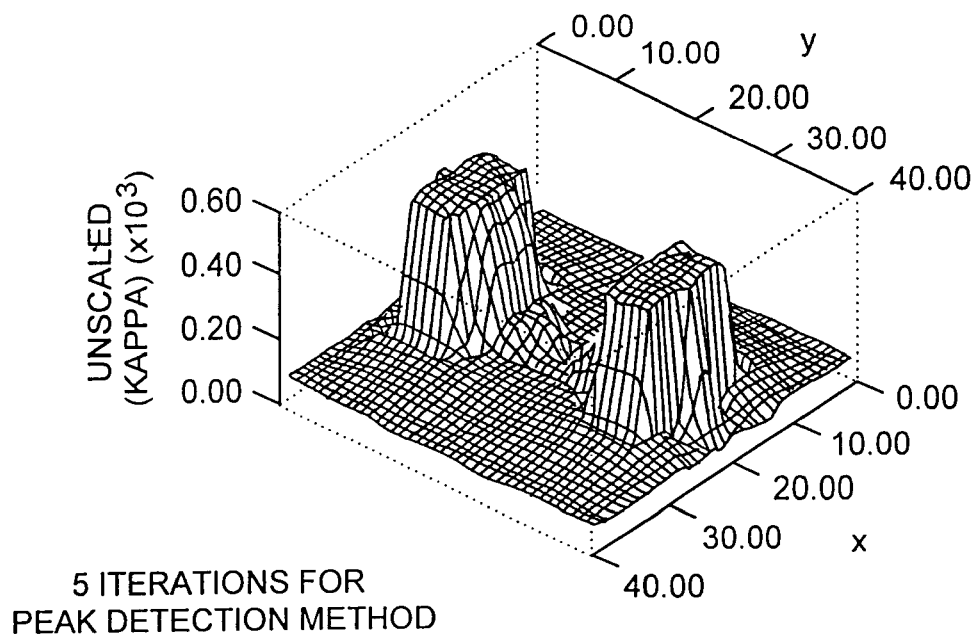
FIGS. 2B and 3B are graphs in three mutually orthogonal axes showing images of conductivity of the objects of FIGS. 2A and 3A produced in accordance with an embodiment of the present invention.
Figure 3B:
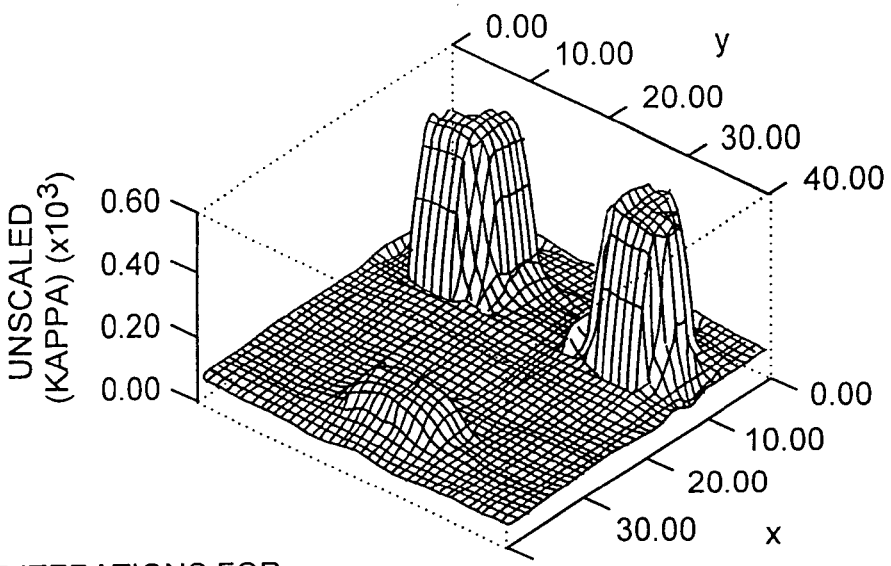

This facilitates image convergence, as well as very rapid resolution, as will be noted below with reference to FIGS. 2B and 3B.

Measurement sets (described as excitations) are obtained by using pairs of electrodes as current electrodes and a selection of the remaining electrodes are used for potential and/or current measurement. Because a unique interpretation is not possible with the results of a single excitation, a number of linearly independent excitations are employed. In theory, a gradient optimization scheme, or a Newton-Raphson scheme, could be used to adjust an assumed internal conductivity distribution in order to minimize the difference between the calculated and the measured voltages over the surface. One disadvantage to these schemes is that such procedures produce dense matrices of order corresponding to the number of nodes employed. For problems with more than a few dozen nodes, this optimization procedure becomes impossibly lengthy. Fine definition cannot be achieved in this way.

Attempting to control the interior conductivity distribution from the outer surface (i.e. remotely) results in an ill-conditioned system with consequent numerical instabilities. This is akin to controlling the position of the long end of a meter stick with a fulcrum 1 cm from the short end where the finger is applied.

In the peak-detection method of the present invention, a definition of the neighbourhoods, i.e. of the "hills" and "valleys", is obtained, to which the acceleration method is applied. The boundaries are ill-defined by a straightforward application of a double-constraint, error-function minimization method. In the Peak Detection Method (PDM) of the invention, threshold criteria are utilized, between low and high-value regions, to determine boundaries within which acceleration procedures are applied. This has proven to be very successful. The result is that edges are sharpened and the regions to be detected and displayed are more clearly demarcated, as shown in FIGS. 2A and 2B. FIG. 2A is an image obtained using the method described in the aforenoted Wexler et al. patent, and FIG. 2B, is an image which was produced using the present embodiment after only 5 iterations. Clearly the present invention converges much faster, and to a clearer image than the aforenoted prior art method.

It should be noted that the peak-detection method is a digital image processing procedure that will sharpen images but could have the effect of causing a divergence from physical principles. In order to avoid this effect, it is used in conjunction with the double-constraint method, that embodies the Laplace equation, thus ensuring that the electromagnetic field equations are properly satisfied and that the current-flow paths are accurately determined. This permits (given that efficient methods are employed) very high definition images to be rapidly achieved. Indeed, by the use of regular finite elements, this approach can be generalized to use other object-dependent image processing methods between EIT iterations.

In operation, firstly two field solutions, one for each of the following boundary condition setups, are performed for each excitation pattern:

(a) Inhomogeneous Neumann boundary conditions are applied at each current-excitation point and homogeneous boundary conditions at points along the boundary where no electrodes are applied and with a reference ground potential applied at one or more points; and (b) Dirichlet boundary conditions, with measured voltage values and with a reference ground potential, are applied at one or more points and with inhomogeneous boundary conditions applied at each current-excitation point.

For convenience, these field solutions are termed the Neumann and Dirichlet solutions respectively. The field solutions are found through the solution of the Poisson equation:

$$-\nabla \cdot \kappa \nabla \phi = f \qquad (1)$$

where $\kappa$, $\phi$, and f are the conductivity, electrical potential and impressed current source distributions respectively within the region being studied. The units are $(\text{ohm-m})^{-1}$, volts and Amperes/m$^3$ respectively.

Although, strictly speaking, this equation holds only for the d.c. case, it is applicable to the a.c. case if the conductivity is sufficiently high so that with the inclusion of dielectric effects the resulting wavelength of the signal is significantly larger than the objects being imaged.

The Poisson equation is subject to the following Neumann and Dirichlet boundary conditions, which are respectively:

$$\kappa(s)\frac{\partial \phi}{\partial n}|_s = h(s) \qquad (2)$$

where (s), in Amperes/m$^2$, describes the electrical current flux density entering or leaving the medium over an electrode surface. Where no current is impressed, h(s)=0.

$$\phi(s)=g(s) \qquad (3)$$

which corresponds to the measured potentials over the top surface.

Then Equation (1) is applied to each such pair of solutions for each excitation pattern. However, with boundary conditions corresponding to actual measurements and with the conductivity only an estimate of what actually existed during the measurement, the pair of boundary conditions applied to the solution cannot be expected to produce identical computed internal fields.

The imposition of Ohm's law $$\bar{J}=-\kappa\nabla\phi \qquad (4)$$

where J represents the current density over the interior region employing both the previously estimated current-flow density and potential for all excitations permits a conductivity distribution to be found that yields approximate compatibility of the Neumann and Dirichlet boundary conditions to be attained. To this end, a least-square technique is employed to produce an improved estimate of the conductivity distribution—one that satisfies both boundary conditions, for all excitations, in an average sense. Thus, displacement of the conductivity estimate is caused.

With the current density (as calculated from the potential using the Neumann boundary condition throughout) and the potential (as calculated using applied voltages, i.e. the Dirichlet boundary condition where appropriate), Ohm's law is generally not satisfied. Thus, there is a residual whenever $\bar{J}+\kappa\nabla\phi$ is evaluated. To enforce compatibility, the minimization of the square of the residual over all points and for all excitations is sought. It is therefore sought to minimize $$R=\Sigma_X \int\int\int_V (\bar{J}+\kappa\nabla\phi)\cdot(\bar{J}+\kappa\nabla\phi)dv \qquad (5)$$

where R is the squared residual sum, V is the region over which the imaging is performed, and X represents the excitations over which the sum is taken.

Several numerical methods may be used to accomplish the above operations. We have used the finite element method (FEM). In its simplest form, one may assume a constant ($K_I$ value within each element i) More generally, the conductivity may be allowed to vary within each element in which case the conductivity value needs to be evaluated at several points within each element.

As an example, consider that a three-dimensional grid of nodes is defined over a cube considered to be excised from the host medium and includes the region of interest. The cube is of length l each side and is subdivided into a mesh defined by n points per edge. Thus there are n−1 links or mesh intervals to an edge, each of length $$h=l/(n-1) \qquad (6)$$

Because Equation (5) can be represented as a summation over finite element volumes Vj, it can be written as $$R=\Sigma_x \iiint_V (\bar{J}+\kappa\nabla\phi)\cdot(\bar{J}+\kappa\nabla\phi)dv \quad (7)$$

where $\kappa_j$ represents the conductivity distribution within element j. For purposes of simplicity, it is here assumed that the conductivity is of constant value within each element. However, the algorithm provides for inhomogeneous conductivity values by representing the conductivity as, say, a polynomial distribution within each finite element.

Then, to minimize the residual by adjustment of each conductivity I, set $$\frac{\partial R}{\partial \kappa_i} = 0 \quad (8)$$

in which anti are held at the previously computed values. Then, upon rearranging the equation, $$\kappa_i = \frac{-\sum_x \iiint_{V_i} \bar{J}\cdot\nabla\phi dv}{\sum_x \iiint_{V_i} \nabla\phi\cdot\nabla\phi dv} \quad (9)$$

results. For each point i, the conductivity i is calculated. Equation (9) is referred to as the Wexler Algorithm, The above operation yields a new conductivity value within the region of each element i. Equation (9) is applied over all points at which the conductivity $\kappa_i$ is desired. With this new set of conductivity values the operation is repeated: new field distributions are calculated using the new conductivity distribution and, consequently, a newer set of conductivities is determined by Equation (9).

Figure 4A:
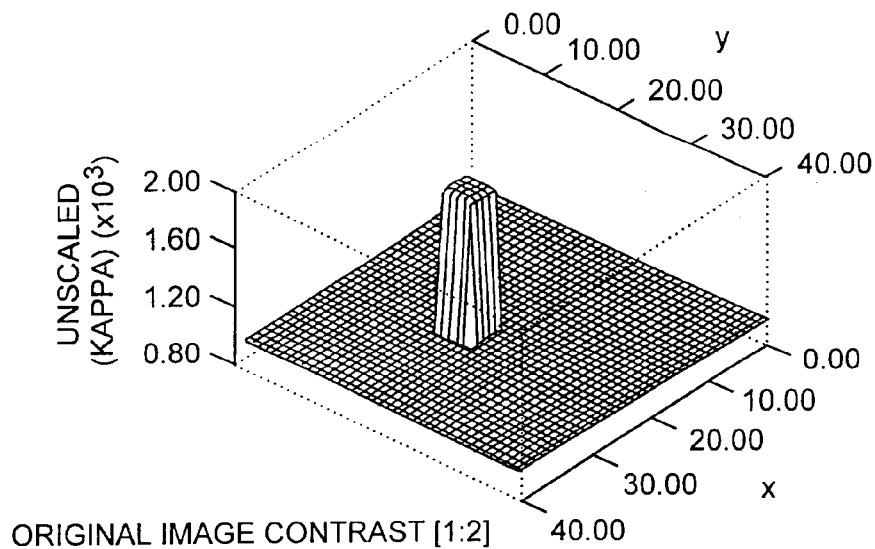
FIGS. 4A, 4B and 4C are graphs in three mutually orthogonal axes showing respectively images of conductivity of an object respectively with original image contrast, an image recovered using a prior art method, and an image recovered using the present invention with the same number of processing iterations as in the prior art method.
Figure 4B:
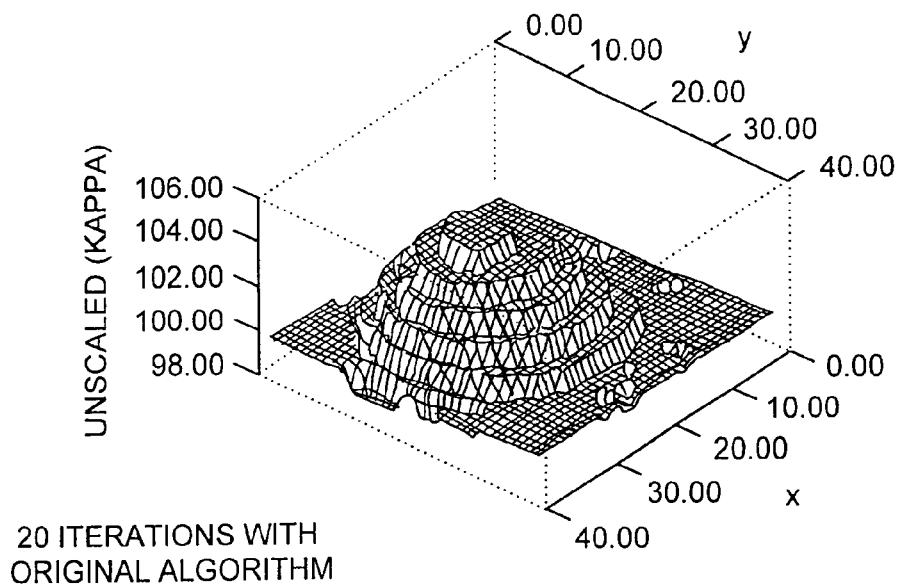
Figure 4C:
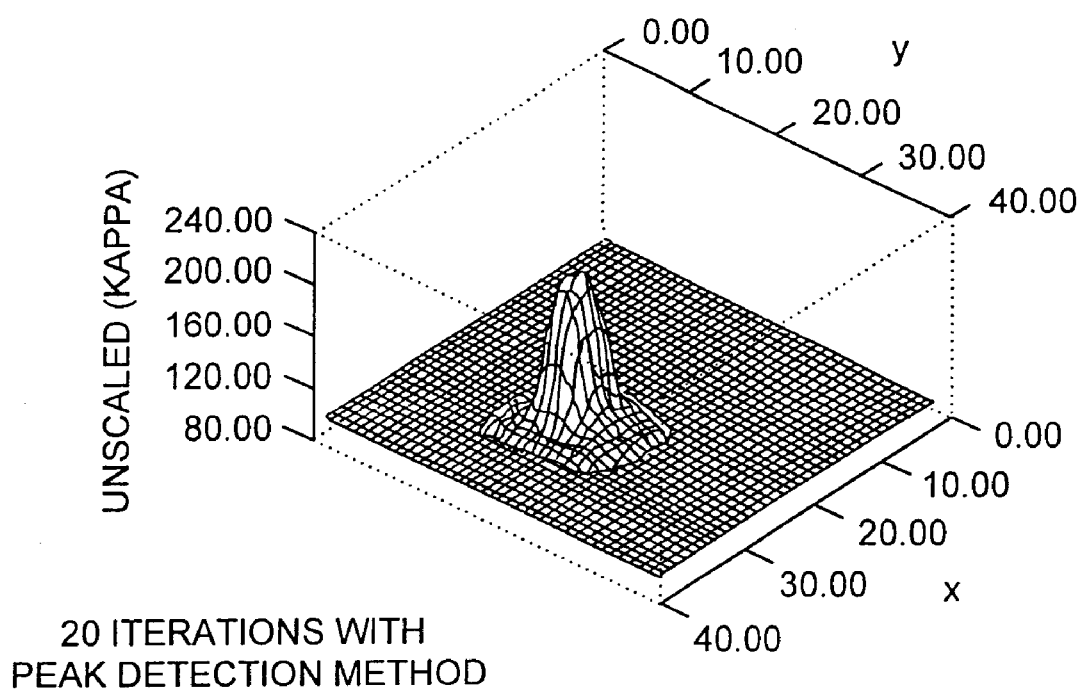

In contrast with other EIT methods, and with reference to FIGS. 4A, 4B and 4C, the prior art method described in the aforenoted Wexler et al. patent casts the problem into the interior by solving the field problem subject to the known boundary conditions (i.e. the Neumann problem with specified applied currents and the Dirichlet problem with known measured boundary potentials). This technique is referred to as the double-constraint method.

An important distinction from other inversion procedures, is that the error to be minimized (by adjustment of the conductivity distribution) is the difference between the interior current densities calculated from the Neumann and Dirichlet problems. Thus the conductivity perturbation, at any point in the interior, is controlled by field solutions near at hand rather than by long-distance. Additionally, because of the local control, the resulting matrices are sparse. This means that a great number of variables may be accommodated and the imaged object may be very well-defined. Furthermore, the error to be minimized is a squared sum over the whole region for all excitations. The process is a least-square process which carries with it a measurement-error averaging property as well as stability.

Using the above procedure, i.e. the double-constraint method of the aforenoted Wexler et al patent, a large number of iterations may be required with consequent lengthy computation times to achieve a well defined image. As shown in FIG. 4B, this method of 20 iterations has not yet produced a well defined image. In such an iterative computation, the successive or simultaneous overrelaxation procedure $$\omega(\kappa_i^{(n+1)}-\kappa_i^{(n)})+\kappa_i^{(n)} \Rightarrow \kappa_i^{(n+1)} \quad (10)$$

is used to accelerate convergence of the equation solution. The iteration count is indicated by the superscript.

However, the application of Equation (10) over all of the conductivity nodes usually fails to greatly reduce the number of iterations required (i.e. a large number of potential and then conductivity iteration loops are still required) or may fail to result in convergence. It does not produce an image with sharp edges in a reasonable time.

We have now found that the successive or simultaneous overrelaxation procedure will converge rapidly when applied specifically to regions where localized hills and valleys are found to be emerging (i.e. the Peak-Detection Method herein as shown in FIGS. 2A, 2B, 3A and 3B).

Figure 6:
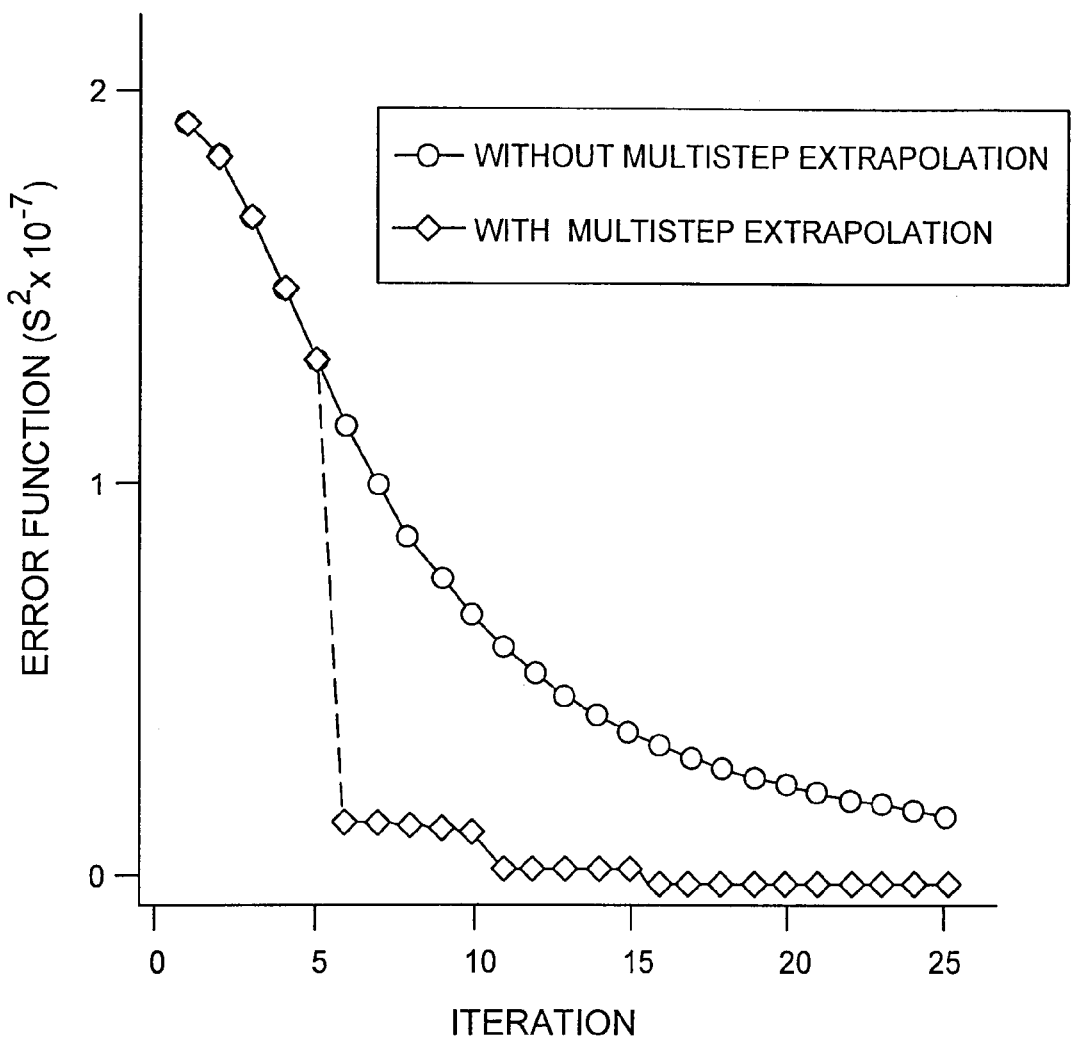

We have found that alternatively, acceleration of the process may also be induced by determining the pattern of convergence, approximating this pattern with an appropriate function, and then extrapolating the functional behaviour to the limit of an infinite number of iterations (i.e. the Multistep Extrapolation Method herein as shown in FIG. 6).

These methods to accelerate the imaging process are described in more detail below.

The Peak-Detection Method

Whether in two-dimensional or three-dimensional regions, a peak value of a hill (which should be construed to include the inverse of a hill or valley) is located by scanning the data. An average value of conductivity in the surrounding region (which could include the entire remaining region) is calculated. Then, preferably, if the hill has a value greater than the surrounding terrain, a bounding surface is defined where the conductivity is, for example, 20 percent of the surrounding terrain-to-hill value above the adjacent terrain. This is treated as a threshold value. Then Equation (10) is applied only to those nodes within the hill region. Likewise, the procedure is applied to enclosed valleys.

Typically, from experience, the acceleration factor ω taken in the range 1–1.5 has yielded good results.

To sharpen the hill, once several applications of the acceleration procedure have been employed, the threshold is increased to sharpen the bounding surface locations. It has been found that a gradual increase to a 50 percent threshold value yields good results.

This has proven to be very successful. The result is that edges are sharpened and the regions are more clearly demarcated, as shown in FIGS. 2B and 3B, which was produced by only 5 iterations. Clearly, the present invention resolves images much faster, and to a clearer image than the aforenoted prior art method.

Imaging in a two-dimensional region, with the peak-detection method, involves defining a region to be accelerated by a curve in the two-dimensional space. By extension, in three-dimensional space, the region would be defined by a surface in three-dimensional space. This is a direct extension. To define the three-dimensional regions (of hills and valleys) to which acceleration is to be applied, bounding surfaces are located using previously described threshold value approximation as part of the iterative procedure. But, as a matter of programming and computational convenience, we bound the object using the two-dimensional threshold value approach applied to three-dimensional planar slices. The region to be accelerated need not be precisely demarcated and so we have found this approach to be adequate. Nonetheless, the imaging problem is solved as a fully three-dimensional problem.

It should be noted that the peak-detection method is a digital image processing procedure that will sharpen images but could have the adverse effect of causing a divergence from physical principles. In order to avoid this effect, it is preferred that it should be used in conjunction with the double-constraint method, that embodies the Laplace equation, thus ensuring that the electromagnetic field equations are properly satisfied and that the current-flow paths are accurately determined. This permits (given that efficient field-solving methods are employed) very high definition images to be rapidly achieved. Indeed, by the use of regular finite element methods, this approach can be generalized to use any of several object-dependent image processing methods between EIT iterations.

The Multistep Extrapolation Method

In accordance with another embodiment, the displacements of the conductivity value at each conductivity-calculation stage is tracked. The displacement value, at each node at which the conductivity is calculated, is evaluated. Then, a number of functions are examined to find the one (called the characteristic equation) that best describes the behaviour of the displacement norm as a function of iteration count. We have found the following equation to describe very well the behaviour of the converging pattern (and, likely, others may be used as alternatives) of the conductivity (or specific impedance, generally) convergence behaviour:

$$a_0 + a_1/\sqrt{(n)} + a_2/(n)^{3/2} + a_3 \log(n)/n^2 \tag{11}$$

where n is the iteration count. The coefficients are determined by fitting this (or another) equation to the data. Then $a_0$ is the ultimate conductivity value approximated on the basis of the employed conductivity values. Once a set of new and more accurate conductivity values results from this procedure, the procedure may be repeated as many times as required. FIG. 6 shows the error function reduced rapidly with but two steps of the multistep approximation method. This results in quick convergence to the images such as those shown in FIGS. 2B, 3B and 4C, as contrasted with the images such as those shown in FIGS. 2A, 3A and 4B.

Figure 5:
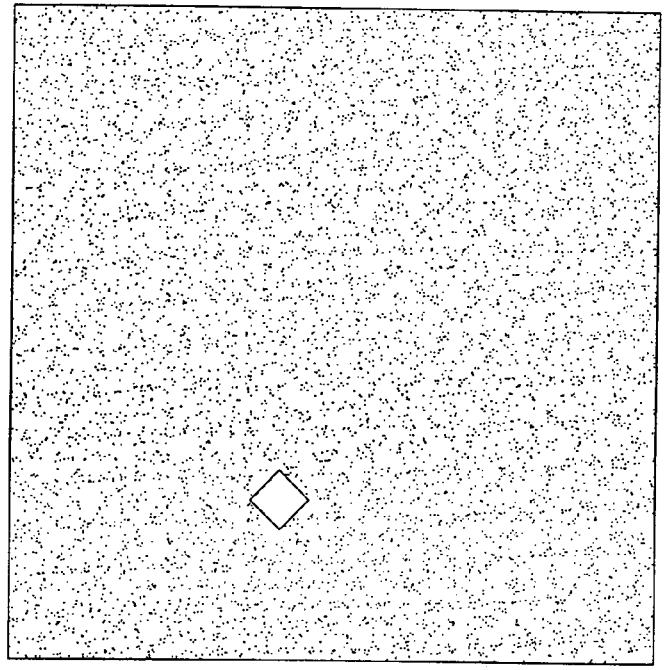
FIG. 5 illustrates a model object, and a resulting image, using the method of the present invention, FIG. 6 are graphs of error function using prior art method and of the present invention, showing how quickly the present invention converges.
Figure 5:
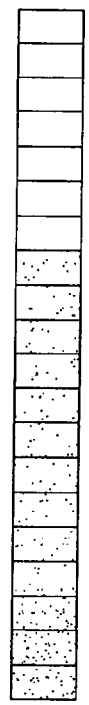
Figure 5:
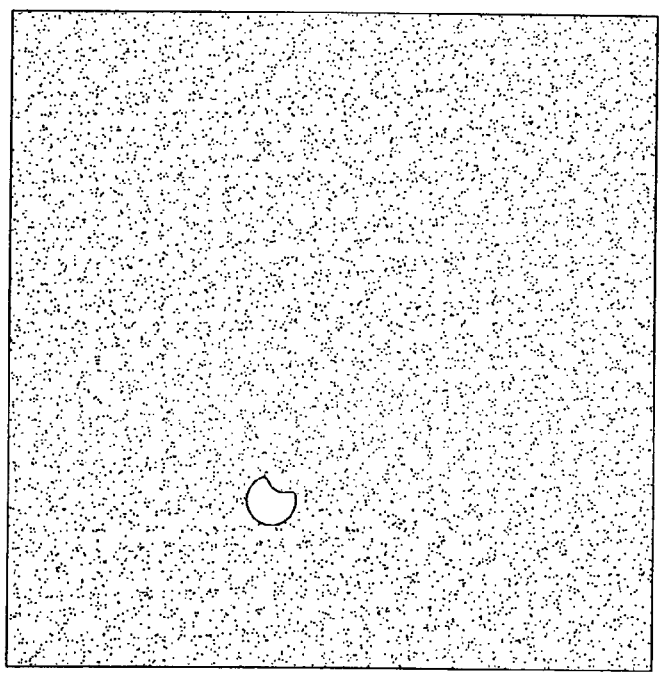

FIG. 5 illustrates a model object, and of a resulting image, using the multistep extrapolation method of the present invention.

The speed of convergence is also clear from the graphs shown in FIG. 6, which shows an error function according to the prior art, without the multistep extrapolation method, and with two steps of multistep extrapolation in accordance with the present invention.

Figure 7A:
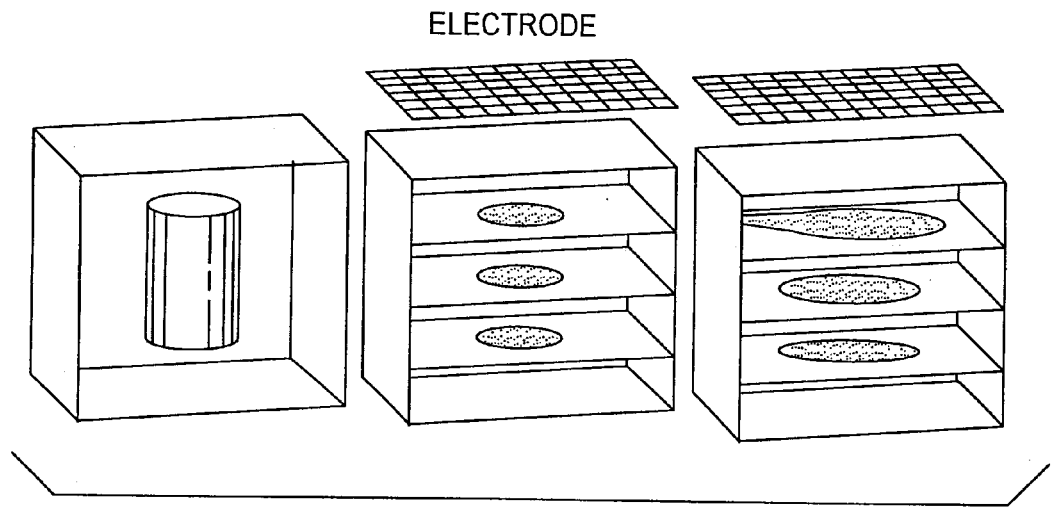
FIGS. 7A and 7B show recovered images using an embodiment of the present invention for a steel barrel buried within sandy soil.
Figure 7B:
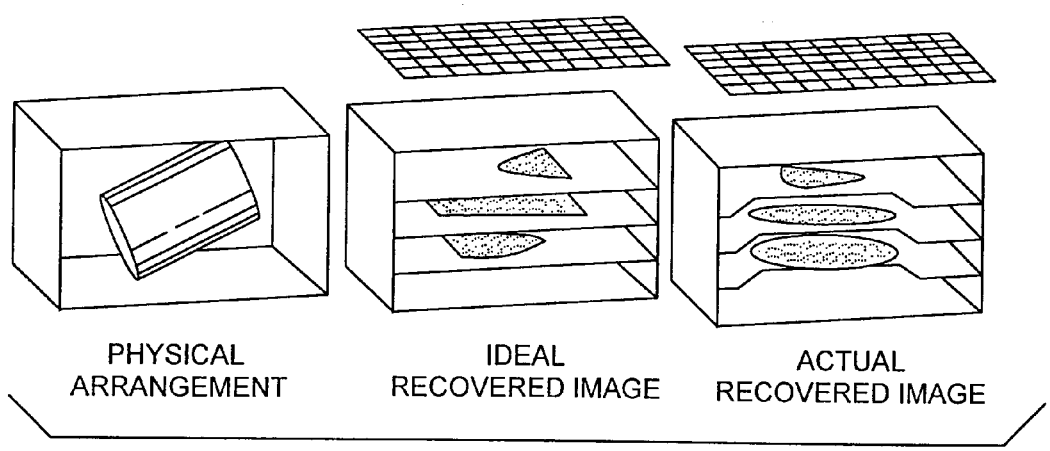

FIGS. 7A and 7B show recovered images for a steel barrel buried within sandy soil. Two orientations of the barrel were employed and an indication of this is provided by the experimental results obtained. FIG. 7A shows a vertical barrel and FIG. 7B shows a tilted barrel. The left image in each of these figures is of the physical arrangements, the center image of these figures show the ideal recovered image, and the right image of these figures are obtained from operation of the method of this invention.

All excitations and measurements were restricted to the top surface of the soil. The current measurements were taken and the data was stored in the personal computer. The imaging method was performed and the graphics were presented by a Silicon Graphics workstation. The image processing was accomplished by the double-constraint method described in the prior art and produced the presented images in 650 iterations. Using the double-constraint method augmented by the peak-detection and the multistep extrapolation methods in accordance with the present invention, the convergence curve indicated convergence in only 5 to 10 iterations. The required convergence count reduction is about two orders of magnitude, thus greatly enhancing the usability of the system.

Modeller-Predictor-Corrector (MPC) Method to Accelerate Convergence

In accordance with another aspect, the displacements of the electrical potential values (and, optionally, the conductivity values as well) at each conductivity-calculation stage are tracked. The displacement values, at each node at which the conductivity is calculated, are evaluated and stored. Then, a function is found that satisfies the least-squared difference (i.e. the residual) in an optimal sense. In other words, the least-squared residual (often called the error) is minimized. The improvement over the Multistep Extrapolation Method described above, is that estimation of potentials and conductivities, with this approach, are likely to be closer to physical reality by virtue of the averaging effect (over the electric potentials and conductivities) rather than to base an extrapolation, with iteration count, upon a single variable (i.e. the conductivity) alone. In this way it is found that the number of iterations required is usually significantly less than that needed for the Multistep Extrapolation Method.

The MPC method is carried out a follows:

Step 1: Model $\phi$ and K as a function of iteration i.

The recovered potential and conductivity distributions, over the first, $2^{nd}$ and $n^{th}$ iterations, are modeled using the nonlinear least-squares filling scheme of Levenberg-Marquardt (LM). The fitted mathematical equations as a function of iteration i, are expressed as:

$$\phi = \phi(i) \tag{12}$$

$$K = K(i) \tag{13}$$

where $\phi$ and K are the potential (or voltage) and conductivity distributions are iteration i respectively.

In order to use the Levenberg-Marquardt least-squares fitting algorithm and to ensure correct "fit parameters" the correct actual physical peak shapes (i.e., the fit functions) for the potential and conductivity distributions history are required. The actual "fit functions" for the conductivity distributions are in nature of types three-parameter exponential or logarithmic functions. The fact that the LM method is an iterative process that requires user-defined "fit-function", any interpretations from the final results are only as good as the initial inputs. After all, the algorithm only optimizes the information fed into it; it can not interpret it for the user.

Step 2: Predict K at iteration I ($K_I$)

Once the optimal equations for potential, $\phi$, and conductivity, K are derived from Step 1, the potential relation is then used to derive the iteration number I, at which the algorithm is considered to have convergence. This is accomplished by substituting the known potential distribution, $\phi_{known}$, obtained through direct measurements, into the mathematical relation (12). Unlike in the multistep approach, where guesses at iteration number are taken repeatedly until convergence, in the MPC method no guess is made. Rather, the known potential ($\phi_{known}$) is used to derive the correct iteration number, I for which the algorithm is considered to converge.

$$\phi_{known} = \phi(I) \tag{14}$$

$$K_d = K(I) \tag{15}$$

Thereafter, the derived number of iterations, I, is used in the conductivity relation (15) to derive the corresponding conductivity distribution ($K_d$). At this stage, it is assumed that the derived conductivity distribution at iteration (I) is equivalent or close to the distribution being sought. The algorithm then goes on to Step 3.

Figure 8:
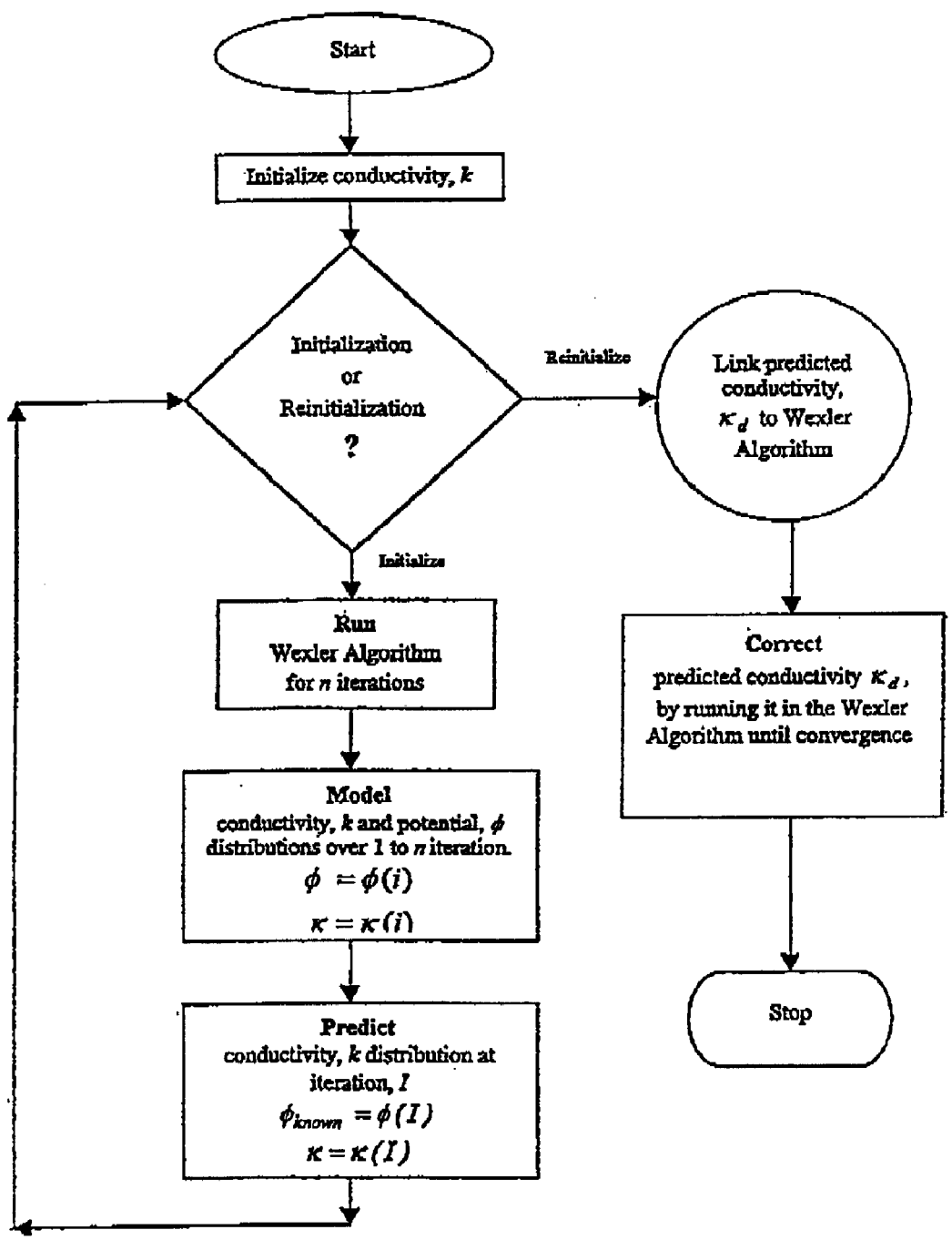
FIG. 8 is a flow chart of the MPC method.

Referring to FIG. 8 there is shown the MPC flow chart. The algorithm is initialized using an assumed conductivity distribution. A decision is then made if it is an initialization or reinitialization procedure. If it is initialization, the algorithm proceeds to the RUN, Model, and Predict steps respectively. The derived conductivity $K_d$, at the end of the Predict stage, gets fed back to the decision phase. At this point, the algorithm recognizes that this is the reinitialization step. This in turn is fed into the Wexler Algorithm for error correction until convergence.

Step 3: Correct $K_d$ by Re-Initializing

The earlier assumption of Step 2, that the derived conductivity distribution ($K_d$) at iteration (I) is equal to the distribution being sought is not entirely incorrect. It is obvious that ($K_d$) was arrived at by some interpolation operations, quite likely it contains some error. To minimize the errors that might have been introduced at Step 1 and 2, the derived conductivity distribution ($K_d$) as the initial starting conductivity distribution in Step 1 of the original Wexler EOT algorithm flow chart. As well as removing any discrepancy, the re-initialization step assures the correct physical approach of the original Wexler EIT image reconstruction algorithm.

The Levenberg-Marquart (LM) Least-Squares Fitting Algorithm

As stated previously, EIT is a nonlinear inverse problem and as such data modelling requires a nonlinear approach. Mathematically, the building blocks of any fitting procedure are:

The data which represent the results of some measurements in which one or several independent (input) variables (x1, x2, x3) were varied over a certain range in a controllable manner so as to produce the measured dependent (output) variable(s) y1, y2, y3.

The mathematical expression (a function or a set thereof) in the form $Y1 f1(x1,x2,x3;p1,p2,p3)$ $Y2=f2(x1,x2,x3;p1,p2,p3)$ $Y3=f3(x1,x2,x3;p1,p2, p3)$ which represents the theoretical model believed to explain the process that produced the experimental data. The model usually depends on one or more parameters, p1, p2, or p3. The aim of the fitting procedure is to find the values of the parameters which best describe the data.

It is necessity to design a figure-of-merit function (or merit function for short) that measures the agreement between the data and the model with a particular choice of parameters. As will be discussed shortly, in the Levenberg-Marquardt (LM) method, the merit function employed is the CHI-Square ($\chi^2$) function. The parameters of the model are then adjusted to achieve a minimum in the merit function, yielding best-fit parameters. The adjustment process is then a problem in minimization in many dimensions. To be genuinely useful, a fitting procedure should provide 1) parameters, 2) error estimates on the parameters, and 3) a statistical measure of goodness of fit. The Levenberg-Marquardt least-squares algorithm satisfies these requirements.

The Levenberg-Marquardt (LM) method is the most widely used alogrithm in nonlinear least squares fitting. It is very useful for finding solutions to complex fitting problems. Basically, the Levenberg-Marquardt method combines the robustness of a steepest descent method with the efficiency of a Gauss-Newton method. The steepest descent and Gauss-Newton methods are comprehensively discussed in Press et al. 1986, Fltcher, 1987, and Reich, 1992. For the purpose of this discussion and its application here, only the key features of the Levenberg-Marquardt algorithm, an algorithm that switches continuously from a gradient method far from the minimum to a Gauss-Newton step as the minimum is approached, are discussed.

As shown by Press et al., 1986, the following quadratic form can approximate a general nonlinear fit equation, $$\chi^2(a) \approx \gamma - d \cdot a + \frac{1}{2} a \cdot D \cdot a$$

where $\chi^2$ is the merit function, the parameter used to determine what the best fit is for varying (a) which is the set of M unknown fit parameters ($a_1$, $a_2$, $a_m$). y is the shape or curve that is being fitted. D is an M×M Hessian matrix, the second partial deriviatives of the functions used for fitting and d is a gradient vector (steepset descent of order M), the first partial derivatives of the functions.

For poor initial approximations, the method of steepest descent will localize the fit parameters by finding the next parameter values ($a_{next}$), using the current fit parameters ($a_{cur}$) via the following equation, $$a_{next}=a_{cur}+D^{-1} \cdot [\nabla \chi^2(a_{cur})]$$

If the initial guess is fairly close, the Hessian matrix method works better for finding the minimized values ($a_{min}$), by using current fit parameters ($a_{cur}$) as shown below, $$a_{min}=a_{cur}-const \times \nabla \chi^2(a_{cur}) \tag{16}$$

upon carrying out the partial derivatives of the merit function, $\chi^2$ and rearranging, a vector ($\beta$) and a matrix ($\alpha$) are derived that represents the fit parameters, $$\beta_k \equiv -\frac{1}{2} \frac{\partial \chi^2}{\partial a_k} \tag{17}$$

$$a_{kl} \equiv \frac{1}{2} \frac{\partial^2 \chi^2}{\partial a_k \partial a_l} \tag{18}$$

After determining the partial derivatives from the gradients, a second derivative term arises, causing a destabilization during the fitting routine. The contribution of the second term, which tends to cancel itself out when summed over all data points (N), can be neglected, simplifying the αkl term. Hence, ignoring the term gives the following for the Hessian matrix, when summed over all the data points in the curve, N, $$a_{kl} = \sum_i^N \frac{1}{\sigma_i^2} \left[ \frac{\partial y(x_i; a)}{\partial a_k} \frac{\partial y(x_i;a)}{\partial a_l} \right] \tag{19}$$

Using the Inverse of the Hessian matrix, the step size can be rewritten as a set of linear equations that can be solved for the new step size, δal, $$\delta a_l = \frac{1}{a_{kl}} \times \beta_k \tag{19}$$

The new step is then added to the current value and tested in the merit equation for "best fit". Similarly, the steepest descent formula of equation (16), translates to, $$\delta a l = \text{constant} \times \beta l \qquad (20)$$

which is then subtracted from the current value to give the new parameters for testing the "best fit". The final "best fit" solution is arrived when $\chi^2$ is at a minimum, or when $\beta k$ values are 0 at all k values. It should be noted that any changes in $\alpha k l$ would not affect the final parameter fit values, since its only purpose is to determine the rate (i.e. the step size) at which the minimum is obtained.

The Levenberg-Marquardt method combines the inherent stability of steepest descent with the quadratic convergence rate of the Gauss-Newton method as described in the previous section. The algorithm uses the method of steepest descent to determine the step size when the results are far from the minimum, $$\delta a_l = \text{constant} \times \beta_l$$

$$\delta a_l = \frac{1}{a_{kl}} \times \beta_k$$

But as the solution approaches the minimum, the algorithm switches to the Hessian matrix for determining the step size in order to zero in on the best fit. Marquardt realized that by combiing equations 12 and 20, the full advantage of both methods can be derived, $$\delta a_l = \sum_{l=1}^{M} \frac{1}{a_{kl}} \times \beta_k \qquad (21)$$

where $\alpha$ is a new matrix obtained by combining 19 and 20 and is defined as, $$a_{jj} \equiv a_{jj}(1+\lambda)(j=1.M) \qquad (22)$$

$$a_{jk} \equiv a_{jk}(j \neq k) \qquad (23)$$

and $\lambda$ ($\lambda >> 1$) is a regularization constant (or fudge factor) to regulate the step size. Marquardt's equation spans the full range of the fitting processes, from the method of steepest descent to the Hessian matrix (or Gauss-Newton) method.

The algorithm is usually implemented as follows:

Compute $\chi^2(a)$;

Guess at a modest value for $\lambda$, say $\lambda=0.001$;

Solve equation 21 for $\delta a$ and evaluate $\chi^2(a+\delta a)$;

If $\chi^2(a+\delta a) \geq \chi^2(a)$, increase $\lambda$ by a factor of 10 (or any other substantial factor); and If $\chi^2(a+\delta a) < \chi^2(a)$, decrease $\lambda$ by a factor of 10 update the trial solution.

The alogorithm iterates until some convergence criteria is reached. Typically this means when a minimum in the reduced $\chi^2$ is reached.

The LM method works very well in practive and has become the standard of nonlinear least-square routine. The Levenberg-Marquardt scheme is implemeneted in Step 1 of the Modeller-Predictor-Corrector to model potential (voltage) and conductivity distributions from a knowledge of their past history and an idea of their correct actual physical peak shapes (i.e. the fit function).

3-D Computer Simulations Using the MPC Algorithm

In order to demonstrate the effectiveness of the Modeller-Predictor-Corrector (MPC) scheme in improving convergence rate of the original Wexler 3-D EIT algorithm, the previous 3-D simulation of small breast tumour imaging is repeated with the MPC scheme.

Figure 9:
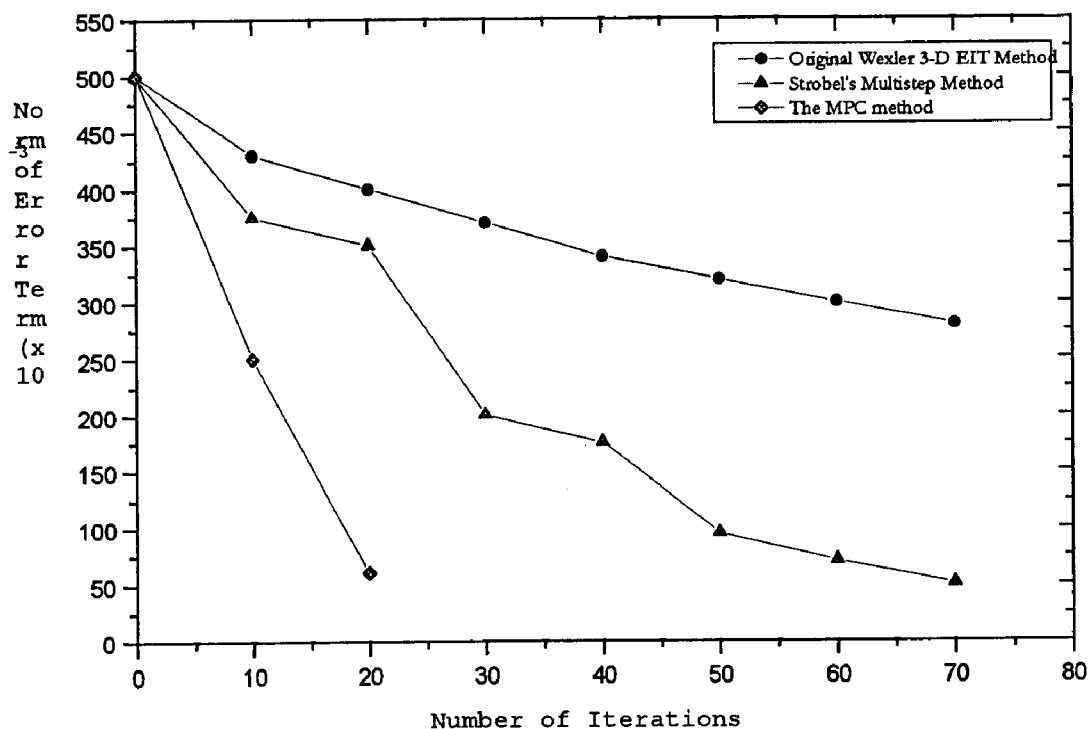
FIG. 9 is a graph illustrating convergence for three different methods.

The modelling is done over the first two to fifteen iterations, conductivity and potential distributions are predicted at the $15^{th}$ iteration, and the correction is done over the next five iterations (i.e. a total of 20 iterations for an approximate time of 7.4 minutes). To demonstrate and compare its ability in improving convergence rate, a comparison to the original Wexler and multistep approach of Strobel, 1996 is provided. FIG. 9 shows the error norm plot as a function of iteration count for the original Wexler, Strobel's multistep, and the MPC methods employed here.

It is obvious from FIG. 9 that the MPC algorithm allows fast and quite accurate recovery of conductivity distribution. Though the image recovered by the multistep approach is close to that recovered using the MPC scheme, the time to converge (approximately 16.3 minutes) was much longer that the MPC scheme. At 20 iterations, for a time period of 7.4 minutes, on a SUNW, SPARCstation-4, the recovered conductivity distribution, obtained using the MPC algorithm, was determined to be quite close to the exact conductivity distribution. Using the concept of the conductivity profile matching ratio $\tau$ ($0<\tau \leq 1$), the T value for the original, multistep, and MPC method were determined to be equal to 0.35, 0.78 and 0.82 respectively. The difference between the MPC recovered conductivity distribution to that of the exact distribution was identified to be at the diseased-to-normal tissue interface. Measurement of full width half maximums FWHM's on the recovered image at 20 iterations in the cross-sectional and axial plane were 6.2% and 7.1% of the diameter of the imaging region respectively. These results were an improvement over the original algorithm with FWHMs values of 13.0% and 14.6% in the cross-sectional and axial plane for the central tumour respectively.

Once modeled, the potential and conductivity relations were used to derive the conductivity distribution at which the algorithm will converge or be relatively close to convergence. To minimize errors that may have propagated as a result of the interpolation operations performed on the relations, in an attempt at deriving the conductivity distribution was used to reinitialize the original Wexler algorithm. This ensures that the correct physical approach of the Wexler algorithm is employed. Locator Compensator (LC) Method to Improve Spatial Resolution.

Locator Compensator (LC) Method to Improve Spatial Resolution

In an attempt to improve the original Wexler EIT algorithm, Condamines and Marsili, 1994 observed that the algorithm provides good qualitative results but is quantitively less accurate. Simply stated, the algorithm locates the region(s) of interest (i.e. tumour(s)) at a very low iteration count, irrespective of the size and type (e.g. benign or malignant) of the region(s). However, the recovered conductivity distribution, at such early iteration, is somewhat far from what is desired (i.e. what is being sought).

For EIT to be of clinical potential and for an accurate diagnosis, breast lesion ought to detected at an early stage, physically equivalent to an approximate size of 1–2 mm. Thus, it appears that the spatial resolution that can be obtained with the original Wexler algorithm is not suitable to image small breast tumours. As such, this disclosure focuses on improving the algorithm's present limit of spatial resolution and attempts to refine its ability to detect small breast lesions. A novel algorithm, teamed the Locator-Compensator (LC) algorithm, is developed and implemented on realistic 3-D computer simulations of small breast tumour imaging. Results of simulations are discussed and summarized.

The overall resolution and in particular, the spatial resolution at normal-to-diseased tissued interface would need to be improved. The higher conductivity magnitude of the tumour element/voxel has an undesired effect on the surrounding normal element(s). This, in turn, contributes to the deterioration of image quality at sharp edges. The Locator-Compensator developed here mainly addresses he issue of lower spatial resolution at sharp edges.

How to locate these region(s) of interest and bow best to apply the resolution compensation? An approach that combines en image processing technique, the peak detection method, to locate the region(s) or peak(s) of interest with a modified conductivity distribution-updating scheme is disclosed herein. Although, this method was correct, the results of its implementation on the Wexler EIT algorithm are not appropriately effective in increasing spatial resolution, in particular at normal-to diseased tissue interface, where no drastic improvements were noticeable.

The Locator-Compensater (LC) Algorithm

Despite the selective peak(s) localization approaching attempting to improve spatial resolution, only tumours of physical size >30 mm in diameter could be resolved. At such size, the metastatic probability is substantially high. As discussed earlier, ideal detection size would be within the range of 1–2 mm. Can the original Wexler EIT image reconstruction algorithm be improved to resolve tumours of size <4 mm A novel scheme, the Locator-Compensator (LC) method, developed here appears to do just that!

The Locator-Compensator (LC) algorithm is a combination of a variant of the peak detection method described above and a new resolution compensation scheme. The Locator-Compensator method is discussed in more detail in the next paragraph. In brief, the peak detection variant method is used to locate the spatial coordinates of the peak(s) at early iterations. Location of peaks is done in a much different manner than described above. Once the coordinates of the peak(s) are localized, then the resolution (i.e., in terms of conductivity magnitude of the peak(s)), are compensated. The compensation is performed by applying the original Wexler EIT conductivity-updating scheme over the localized regions rather than over the whole imaging region.

In this implementation of the peak detection method, rather than having to assume a percent of the background conductivity (i.e.,*κb) which subsequently is used as the basis for the criterion for peak detection (i.e., by comparing *κb to Δκ), the variant of the peak detection method employs a non subjective approach for peak(s) localization. The Wexler algorithm with its original conductivity updating-scheme is used to sweep though an imaging region for n iterations. The recovered conductivity distribution at each iteration (i.e.,κ1, κ2, κ3, . . . ,κn) is averaged over n iterations (i.e., κ1+κ2+κ3+. . . +κn/n). The averaged conductivity distribution at n iteration (i.e., κn) is then averaged over all the elements within the imaging region. This result is an average conductivity per element (κen=κn/N), N being the total number of elements in the adopted mesh for image recovery (or solution of the inverse problem). Peaks are located by comparing κen to κen+1, where κen+1, is the conductivity of each element at n+1 iteration. If κen+1>κen, the element or an aggregate of element is/are identified as peak(s). To avoid detecting any unwanted anomalies due to truncation or discretization, a filtering scheme is applied prior to peak(s) detection. Once element (s) is/are identified as peak(s), the spatial coordinates of the immediate elements surrounding the peak(s) elements) are identified. It is at these coordinates that the new conductivity distribution updating-scheme is implemented to compensate for loss in spatial resolution.

Once identified, the calculated potentials at coordinates of identified element(s)are then substituted by the interpolated interior potentials obtained from measured or known surface potentials. The interpolated potentials applied to the surrounding elements nodes of the peak(s) elements caused the interior potentials (i.e., potentials (i.e. potentials at nodes within the localized region(s)) to be nudged in the correct direction (i.e., toward minimization of the differences between the measured and the calculated potentials). Since the localized region(s) would generally consist(s) of a few elements (i.e., pixels or voxels), this selective conductivity-updating scheme is relatively fast and effective. While conductivity in the localized region is updated with the localized updating scheme just described, conductivity update for the rest of the imaging region proceeds via the original Wexler EIT conductivity-updating scheme. This process continues until measured and calculated potentials are equal (i.e., until convergence is attained).

The Locator-Compensator Algorithm is Summarized m the Following Steps:

Step 1. Run Wexler Algorithm for n Iterations

The original Wexler EIT algorithm, with its conductivity updating scheme is used to sweep through the imaging region for n iterations. In brief, the revised estimate of conductivity within element i over all node points and over all excitations is, $$K_i = \frac{-\sum_x \int\int\int_{vi} \bar{J} \cdot \nabla\phi dv}{\sum_x \int\int\int_{vi} \nabla\phi \cdot \nabla\phi dv} \quad (24)$$

where J is the estimated electrical current density distribution, ϕ is the potential obtained with Dirichlet boundary conditions, $K_i$ is a revised estimate of the conductivity within element i, vi is the volume of the element i, and X represents the excitations over which the sum is taken.

Step 2. Save Conductivity Distribution (K) over 1 to n Iterations

The recovered conductivity distribution over the period of iteration 1 to n is saved and averaged over n iterations, $K_n$. The average conductivity distribution $K_n$ is then averaged over all the elements, $K_{en}=K_n/M$. The average over all elements $K_{en}$ is then used as a criterion component for peak(s) detection.

Step 3. Locate Peak(s) with the Peak Detection Variant Method at n+1 Iterations

Peak(s) is/are located by comparing Ken to $K_{en+1}$, where $K_{en+1}$, is the conductivity of each element at n+1 iteration. If $K_{en+1}>K_{en}$, the element or an aggregate of element is/are identified as peak(s) or if $K_{en+1}<K_{en}$, then the element or an aggregate of element is/are not regarded as peak(s). To avoid detecting any unwanted anomalies due to truncation or discretization, a filtering scheme is applied prior to peak(s) detection. Once the peak(s) is/are located, the Immediate surrounding elements nodes spatial coordinates are identified. The potentials at these nodes are saved accordingly.

Step 4. Compensate for Resolution at (n+2) to N Iterations

When viewed as a whole, the imaging region can be considered to consist of localized peak(s) region and a background region. The conductivity updating-scheme for the background region is that as utilized by the original Wexler algorithm, described mathematically by relation (24)

above. The new conductivity updating scheme for the localized region(s) can be arrived at by applying the original Wexler conductivity updating scheme to the identified region(s). In this new approach, the calculated potentials at the spatial coordinates of the external nodes of the elements identified in Step 3 are substituted by the interpolated calculated potentials obtain from the measured or known surface potentials. Tim is to say applying Dirichlet boundary conditions to the localized regions while leaving the remaining initial (i.e., at n+1 iterations) Neumann boundary conditions unchanged. This causes the interior potentials to be nudged in the correct direction. This is performed for every iteration mid over the whole imaging region iteratively until convergence at iteration N. Similarly, the Dirichlet boundary condition for the localized region(s) is, $$\phi(ls)=g(ls) \quad (25)$$

which corresponds to the interpolated calculated potentials at external nodes coordinates of element(s) identified in Step 3. In addition the boundary conditions must include the Neumann conditions at current-injection sites as described in.

The revised estimate of conductivity within element I over the volumetric region enclosed by the identified node points coordinates and over all excitations is given as, $$K_l = \frac{-\sum_x \int\int\int_{vl} \overline{J} \cdot \nabla \phi_l dv}{\sum_x \int\int\int_{vl} \nabla \phi_l \cdot \nabla \phi_l dv} \quad (26)$$

where $\overline{J}$ is the estimated electrical current density distribution, $\phi_l$, is the interpolated calculated potential obtained from the measured or known surface potentials (i.e., from application of Dirichlet boundary conditions), $K_l$, is a revised estimate of the conductivity within element l of the localized region, $v_l$, is the volume of the element l, and X represents the excitations over which the sum is taken.

By combining equations 25 and 26, a new conductivity-updating scheme is obtained. This revised scheme is applied to each element in turn to update the conductivity distribution over the entire region within which the imaging is being performed.

$$K_{i+l} = \frac{-\sum_x \int\int\int_{Vi} \overline{J} \cdot \nabla \phi dv}{\sum_x \int\int\int_{Vi} \nabla \phi \cdot \nabla \phi dv} + \frac{-\sum_x \int\int\int_{Vi} \overline{J} \cdot \nabla \phi_l dv}{\sum_x \int\int\int_{Vi} \nabla \phi \cdot \nabla \phi_l dv} \quad (27)$$

The Locator-Compensator algorithm makes use of the combined updating scheme (27) to recover conductivity distribution. Characteristically, the fact that the original Wexler algorithm locates the peak(s) at early iteration, application of the LC algorithm, will in theory, ensures that the peak(s) converge(s) much faster and with adequate resolution at diseased-to-normal tissue interface. In the next section, the Locator-Compensator (LC) method scheme is tested by performing computer simulations.

3-D Computer Simulations Using the LC Algorithm

Figure 10:
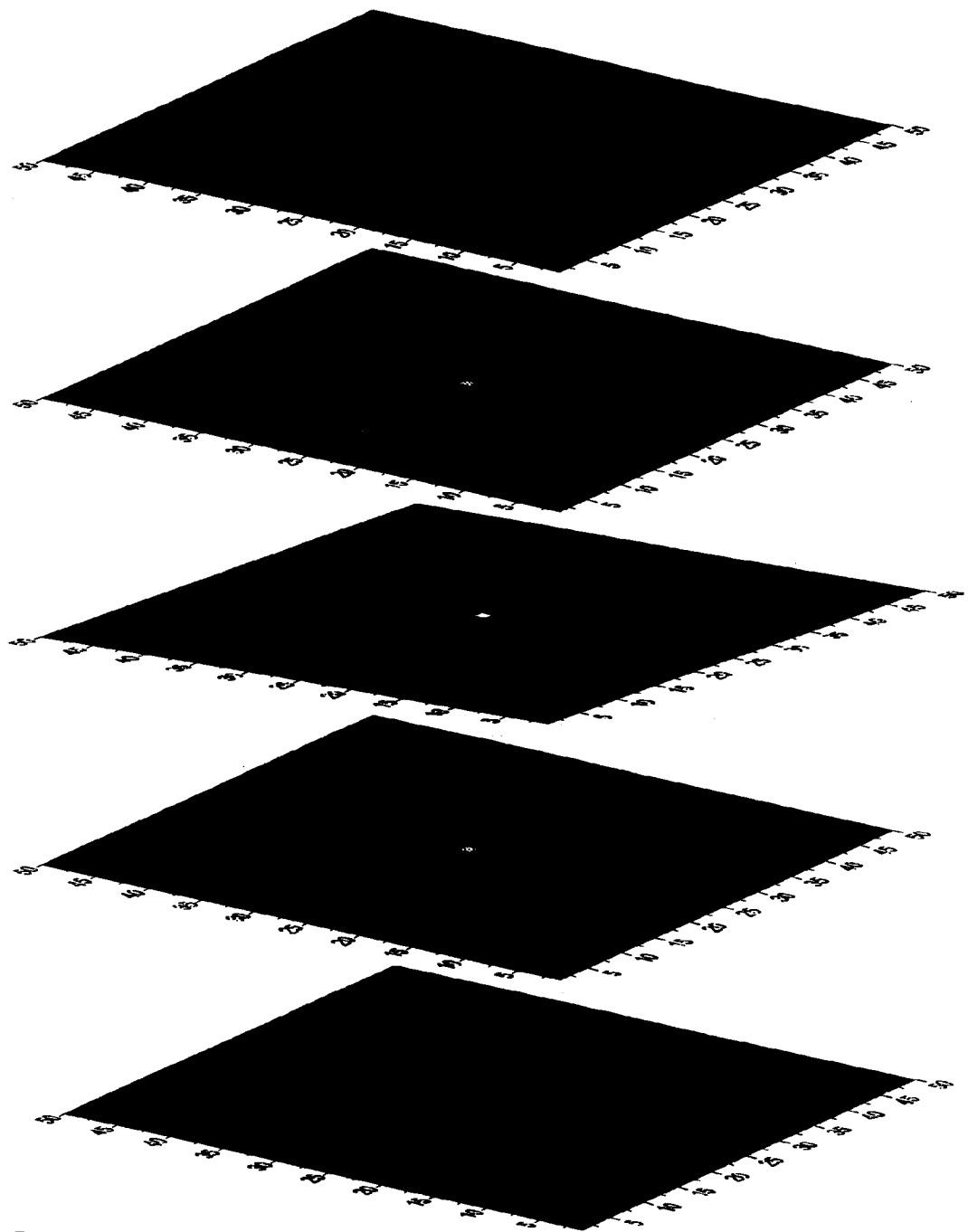
FIG. 10 illustrates recovered images of layers.

To demonstrate the effectiveness of the Locator-Compensator (LC)scheme in improving spatial resolution, in particular at diseased-to-normal tissue interface, the previous 3-D simulation of small breast tumour imaging described above and is repeated here. The original Wexler 3-D EIT algorithm is run for a period of 15 iterations. The recovered conductivity distributions over that time interval are averaged. The averaged distribution is then subsequently average over all the elements. This is saved accordingly and the original Wexler algorithm is allowed to run for one more iteration. At 16th iterations, the average conductivity per element is then used as a criterion to locate peaks. Once localized, the peaks conductivities are then compensated at the 17th iterations by the combined conductivity-updating scheme described above. FIG. 10 shows the recovered images of layers 11, 12, 13, 14, and 15 for the central tumour voxel using the LC algorithm at 50 iterations. The spatial resolution (or the FWHMs) in the cross sectional and axial planes for the recovered image of the tumour voxel are approximately 5.4% and 6.3% of the diameter of the imaging region.

Using simulations, the original Wexler 3-D EIT algorithm was identified to have low resolution. From observations made earlier it appears that the "Tumour-Edge" effect is responsible for the observed low resolution at the edges. As such the Locator-Compensator (LC) method was developed to improve the overall spatial resolution.

In brief, the LC method involved locating the peaks with a variant of the peak detection image processing algorithm and subsequently applying a new conductivity updating scheme. This combination appeared to improve resolution at diseased-to normal tissue interface. Measurement of FWHM's on the recovered images at 50 iterations in the cross-sectional and axial plane were 5.4% and 6.3% of the diameter of the imaging region respectively. These results were an improvement over the original algorithm with FWHMs of values 13.0% and 14.6% in the cross-sectional and axial plane respectively.

It should be noticed that the recovered image resolution obtained from the LC algorithm is higher than that obtained with the Modeller-Predictor-Corrector (MPC). The resolution for the MPC in the cross-sectional and axial planes was 6.2% and 7.1% respectively. Though, the resolution of the LC method is superior to that of the MPC, the LC takes much longer to converge. The MPC converged in 20 iterations while the LC converged in 50 iterations for the same computer simulation setup. If combined, one anticipates that the MPC would help to improve convergence rate and the LC method would improve resolution, in particular, at diseased-to-normal tissue interface.

The spatial resolution of the original Wexler EIT imaging algorithm was demonstrated to be relatively low, compared to other clinical imaging modalities. The spatial resolution was identified to be space variant. The Locator-Compensator (LC) algorithm was developed to compensate for the loss in spatial resolution at diseased-to-normal tissue interface. Improvements were demonstrated on simplified 3-D computer simulations of early breast tumour imaging. It was shown that the LC method could resolve approximately 5.4% and 63% of the diameter of the imaging region.

A person understanding this invention may now conceive of alternative structures and embodiments or variations of the above. All those which fall within the scope of the claims appended hereto are considered to be part of the present invention.

We claim:

1. A method of imaging an object contained in a medium, having a specific impedance which is different from the specific impedance of the medium, comprising steps:
   a) applying current to the medium at various locations at a surface of the medium,
   b) extracting current at other locations,
   c) detecting voltages produced by the current which has passed through the medium from the surface of the medium at various other locations,
   d) determining a region in the medium in which the object is located from values of the detected voltages, e) successively determining a location and shape and conductivity of the object with increasing accuracy by processing values of the detected voltage, f) determining a pattern of convergence, g) selecting an appropriate function which approximates the determined pattern, h) extrapolating the function to a limit of aria infinite number of iterations, and i) displaying an image illustrating the extrapolated function on an axis at locations of the pattern of convergence, wherein steps d), f), and i) further includes:

(aa) modeling recovered voltage and conductivity distributions using the non-linear least-squares fitting scheme of Levenberg-Marquardt iteratively, (bb) deriving the iteration number from step (aa) and substituting the voltage distribution into the model, thereafter using the derived number of iterations to derive the conductivity distribution, (cc) correcting the derived conductivity distribution by re-initializing step (aa) using the derived conductivity distribution and (dd) recursively adjusting the parameters of the model to obtain the best fit parameters.

2. A method as defined in claim 1 including determining and displaying two dimensional image slices of adjacent portions of the medium so as to form a three dimensional image of the object in the medium.

* * * * *